(12) United States Patent
Burgi (10) Patent No.: US 8,961,528 B2
(45) Date of Patent: Feb. 24, 2015

(54) OFFSET CUP IMPACTOR WITH A GRASPING PLATE FOR DOUBLE MOBILITY IMPLANTS

(75) Inventor: Jonas Burgi, Moutier (CH)

(73) Assignee: Greatbatch Medical S.A., Clarence, NY (US)

( * ) Notice: Subject to any disclaimer, the term of this patent is extended or adjusted under 35 U.S.C. 154(b) by 2 days.

(21) Appl. No.: 13/219,767

(22) Filed: Aug. 29, 2011

(65) Prior Publication Data

US 2012/0053592 A1    Mar. 1, 2012

Related U.S. Application Data

(60) Provisional application No. 61/377,701, filed on Aug. 27, 2010.

(51) Int. Cl.
   *A61F 2/34*    (2006.01)
   *A61F 2/46*    (2006.01)
   *A61F 2/30*    (2006.01)
   *A61F 2/32*    (2006.01)

(52) U.S. Cl.
   CPC ..... *A61F 2/4609* (2013.01); *A61F 2002/30426* (2013.01); *A61F 2002/305* (2013.01); *A61F 2002/30565* (2013.01); *A61F 2002/3208* (2013.01)
   USPC .............................................. 606/91; 606/99

(58) Field of Classification Search
   USPC ........... 606/81, 86 A, 86 B, 86 R, 91, 99, 100
   See application file for complete search history.

(56) References Cited

U.S. PATENT DOCUMENTS

| | | |
|---|---|---|
| 1,942,422 A | 6/1931 | Hanna |
| 4,305,394 A | 12/1981 | Bertuch, Jr. |
| D272,648 S | 2/1984 | Bolesky et al. |
| D273,806 S | 5/1984 | Bolesky et al. |
| 4,475,549 A | 10/1984 | Oh |
| 4,520,511 A | 6/1985 | Gianezio et al. |
| 4,528,980 A | 7/1985 | Kenna |
| 4,587,964 A | 5/1986 | Walker et al. |
| 4,632,111 A | 12/1986 | Roche |
| 4,716,894 A | 1/1988 | Lazzeri et al. |
| 4,765,328 A | 8/1988 | Keller et al. |

(Continued)

FOREIGN PATENT DOCUMENTS

| | | |
|---|---|---|
| EP | 0453694 | 10/1991 |
| EP | 0470912 | 12/1992 |

(Continued)

OTHER PUBLICATIONS

European Search Report dated Apr. 4, 2011.

(Continued)

*Primary Examiner* — Todd Manahan
*Assistant Examiner* — Eric S Gibson
(74) *Attorney, Agent, or Firm* — Michael F. Scalise; Steven W. Winn (57) ABSTRACT

An orthopaedic prosthetic inserter used for the implantation of double mobility cup implants is described. The inserter consists of a drive train, a C-shaped housing, and a prosthetic cup engaging subassembly. The subassembly comprises an impaction plate, a grasping plate and a domed nose. When activated by the drive train, a plurality of hook ends extending from the grasping plate latch onto the cup of the prosthetic to hold and manipulate the prosthetic cup during implantation.

29 Claims, 8 Drawing Sheets

(56) References Cited

U.S. PATENT DOCUMENTS

| | | |
|---|---|---|
| 4,904,267 A | 2/1990 | Bruce et al. |
| 4,919,679 A | 4/1990 | Averill et al. |
| 4,921,493 A | 5/1990 | Webb, Jr. et al. |
| 5,019,105 A | 5/1991 | Wiley |
| 5,037,424 A | 8/1991 | Aboczky |
| 5,061,270 A | 10/1991 | Aboczky |
| 5,062,854 A | 11/1991 | Noble et al. |
| 5,089,003 A | 2/1992 | Fallin et al. |
| 5,116,339 A | 5/1992 | Glock |
| 5,124,106 A | 6/1992 | Morr et al. |
| 5,133,766 A | 7/1992 | Halperin |
| 5,169,399 A | 12/1992 | Ryland et al. |
| 5,190,549 A | 3/1993 | Miller et al. |
| 5,234,432 A | 8/1993 | Brown |
| 5,261,915 A | 11/1993 | Durlacher et al. |
| 5,324,293 A | 6/1994 | Rehmann |
| 5,342,362 A | 8/1994 | Kenyon et al. |
| 5,364,403 A | 11/1994 | Petersen et al. |
| 5,417,696 A | 5/1995 | Kashuba et al. |
| 5,443,471 A | 8/1995 | Swajger |
| 5,454,815 A | 10/1995 | Geisser et al. |
| 5,485,887 A | 1/1996 | Mandanis |
| 5,540,697 A | 7/1996 | Rehmann et al. |
| 5,584,837 A | 12/1996 | Petersen |
| 5,658,294 A | 8/1997 | Sederholm |
| 5,665,091 A | 9/1997 | Noble et al. |
| 5,683,399 A | 11/1997 | Jones |
| 5,707,374 A | 1/1998 | Schmidt |
| 5,720,750 A | 2/1998 | Koller et al. |
| 5,863,295 A | 1/1999 | Averill et al. |
| 5,913,860 A | 6/1999 | Scholl |
| 5,976,148 A | 11/1999 | Charpenet et al. |
| 5,993,455 A | 11/1999 | Noble |
| 6,063,124 A | 5/2000 | Amstutz |
| 6,120,508 A | 9/2000 | Grunig et al. |
| 6,197,065 B1 | 3/2001 | Martin et al. |
| 6,432,141 B1 | 8/2002 | Stocks et al. |
| 6,451,058 B2 | 9/2002 | Tuke et al. |
| 6,626,913 B1 | 9/2003 | McKinnon et al. |
| 6,663,636 B1 | 12/2003 | Lin |
| 6,811,569 B1 | 11/2004 | Afriat et al. |
| 7,192,449 B1 | 3/2007 | McQueen et al. |
| 7,335,207 B1 | 2/2008 | Smith |
| 7,341,593 B2 | 3/2008 | Auxepaules et al. |
| 7,396,357 B2 | 7/2008 | Tomier et al. |
| 7,585,301 B2 | 9/2009 | Santarella et al. |
| 7,591,821 B2 | 9/2009 | Kelman |
| 7,604,667 B2 | 10/2009 | DeSmet et al. |
| 7,621,921 B2 | 11/2009 | Parker |
| 7,922,726 B2 | 4/2011 | White |
| 2001/0051830 A1 | 12/2001 | Tuke et al. |
| 2002/0004660 A1 | 1/2002 | Henniges et al. |
| 2002/0116007 A1 | 8/2002 | Lewis |
| 2002/0177854 A1 | 11/2002 | Tuke et al. |
| 2002/0193797 A1 | 12/2002 | Johnson |
| 2003/0009234 A1 | 1/2003 | Treacy et al. |
| 2003/0050645 A1 | 3/2003 | Parker et al. |
| 2003/0083668 A1 | 5/2003 | Rogers et al. |
| 2003/0088316 A1 | 5/2003 | Ganjianpour |
| 2003/0187512 A1 | 10/2003 | Frederick et al. |
| 2003/0220698 A1 | 11/2003 | Mears et al. |
| 2003/0229356 A1 | 12/2003 | Dye |
| 2004/0186586 A1* | 9/2004 | Seyer et al. ................ 623/22.12 |
| 2004/0215200 A1 | 10/2004 | Tomier et al. |
| 2005/0038443 A1 | 2/2005 | Hedley et al. |
| 2005/0075736 A1 | 4/2005 | Collazo |
| 2005/0137603 A1 | 6/2005 | Belew et al. |
| 2005/0171548 A1 | 8/2005 | Kelman |
| 2005/0187562 A1 | 8/2005 | Grimm et al. |
| 2005/0203536 A1* | 9/2005 | Laffargue et al. ................ 606/91 |
| 2005/0222572 A1 | 10/2005 | Chana |
| 2005/0228395 A1 | 10/2005 | Auxepaules et al. |
| 2005/0234462 A1 | 10/2005 | Hershberger |
| 2005/0246031 A1 | 11/2005 | Frederick et al. |
| 2006/0052780 A1 | 3/2006 | Errico et al. |
| 2006/0149285 A1* | 7/2006 | Burgi et al. .................... 606/99 |
| 2006/0241781 A1* | 10/2006 | Brown et al. ............... 623/23.43 |
| 2007/0156155 A1 | 7/2007 | Parker |
| 2007/0167952 A1 | 7/2007 | Burgi et al. |
| 2007/0225725 A1 | 9/2007 | Heavener et al. |
| 2007/0270783 A1 | 11/2007 | Zumsteg et al. |
| 2007/0288096 A1 | 12/2007 | Surma |
| 2007/0293869 A1 | 12/2007 | Conte et al. |
| 2008/0004628 A1 | 1/2008 | White |
| 2008/0021481 A1 | 1/2008 | Burgi |
| 2008/0033444 A1 | 2/2008 | Bastian et al. |
| 2008/0077249 A1* | 3/2008 | Gradel ....................... 623/22.15 |
| 2008/0146969 A1 | 6/2008 | Kurtz |
| 2008/0154261 A1* | 6/2008 | Burgi ............................ 606/53 |
| 2008/0243127 A1 | 10/2008 | Lang et al. |
| 2008/0255565 A1 | 10/2008 | Fletcher |
| 2008/0255568 A1 | 10/2008 | Tornier et al. |
| 2008/0262503 A1 | 10/2008 | Muller |
| 2008/0275450 A1 | 11/2008 | Meyers et al. |
| 2009/0112214 A1 | 4/2009 | Philippon |
| 2009/0182334 A1 | 7/2009 | Brehm |
| 2009/0192515 A1 | 7/2009 | Lechot et al. |
| 2009/0240256 A1 | 9/2009 | Smith |
| 2009/0281545 A1 | 11/2009 | Stubbs |
| 2011/0208202 A1* | 8/2011 | Zumsteg et al. ................ 606/91 |

FOREIGN PATENT DOCUMENTS

| | | |
|---|---|---|
| EP | 0535973 | 4/1993 |
| EP | 357302 | 7/1994 |
| EP | 638299 | 2/1995 |
| EP | 1308140 | 5/2003 |
| EP | 1190687 | 7/2004 |
| EP | 1438936 | 7/2004 |
| EP | 1447058 | 8/2004 |
| GB | 2445087 | 6/2008 |
| WO | 9511641 | 5/1995 |
| WO | 0012832 | 3/2000 |
| WO | 0106964 | 2/2001 |
| WO | 2004069107 | 8/2004 |
| WO | 2005044153 | 5/2005 |
| WO | 2006061708 | 6/2006 |
| WO | 2007098549 | 9/2007 |
| WO | 2008128282 | 10/2008 |
| WO | 2009136284 | 11/2009 |
| WO | WO-2010/012648 | * 2/2010 |

OTHER PUBLICATIONS

Partial European Search Report dated Dec. 1, 2011.
Smith & Nephew Polarcut Dual Mobility System, Dec. 2006.

* cited by examiner

OFFSET CUP IMPACTOR WITH A GRASPING PLATE FOR DOUBLE MOBILITY IMPLANTS

CROSS REFERENCE TO RELATED APPLICATIONS

This application claims priority to U.S. provisional application Ser. No. 61/377,701, filed on Aug. 27, 2010.

FIELD OF THE INVENTION

This invention relates to surgical inserters for aiding in installing orthopedic prostheses, and more specifically, to an improved grasping mechanism for installing acetabular implants in the acetabular socket.

BACKGROUND OF THE INVENTION

A double mobility prosthetic cup is a type of acetabular implant that is designed to increase a patient's range of hip mobility. Unlike other types of acetabular implants, double mobility prosthetic cups do not have an opening through the cup portion which allows for easy manipulation during implantation. For example, a rod is typically threaded through the cup opening to the apex of the cup dome where there is typically a threaded hole. This rod is used like a handle with which to control and guide the implant during implantation. Double mobility implants, on the other hand, do not have such an opening and therefore create a challenge in controlling them during implantation. The present invention solves this problem and provides an effective novel means of manipulating the double mobility implant during implantation.

Complicated mechanical devices have crevices and recesses that are difficult, if not almost impossible to clean with ease. Devices that are not properly cleaned and sterilized run the risk of disease transfer from patient to patient following the emergence of certain "prions" that are not killed by normal hospital sterilization and need to be physically removed by washing and rinsing.

During implantation of the prosthetic cup, a great amount of mechanical force is delivered to the cup implant. Generally, an impacting force is delivered to the proximal end of the inserter which is then imparted to the prosthetic cup at the distal end. The application of such mechanical impacting forces could damage the implant cup, particularly a double mobility prosthetic cup implant since these types of cup implants generally lack the mechanical strength to withstand the application of these forces throughout the prosthetic cup.

Furthermore, these double mobility prosthetic cups are precisely machined with smooth surfaces and as such, these implants could become structurally deformed, cracked or scratched during implantation. Such damage to the cup could result in a decrease of mobility for the patient or the need to repeat the prosthetic cup implantation process. The damage could also increase the risk of higher wear rates from the bearing components leading to possible earlier device failure.

Further, in surgical procedures in which access to the treatment site is limited, it is difficult to use current solutions without subjecting the patient to repeated abrasion and tissue trauma when inserting, operating and extracting surgical instruments.

Still further, once the appropriate position of the implant is selected, it is often difficult to ensure that the position does not change upon insertion of the assembly through the incision.

What is needed therefore is a double mobility implant inserter that minimizes the potential of damaging the cup implant during implantation. Further, the present invention provides an inserter that is easily adjustable, operatable, disassemblable, and cleanable. Still further, what is needed is an inserter that enables the surgeon to better maneuver, position and install the double mobility implant in a particular angular orientation.

SUMMARY OF THE INVENTION

The present invention relates to an acetabular inserter that aids a surgeon in controlling the installation of a double mobility acetabular cup prosthesis. The inserter has a housing which encloses a drive train having, at a far end, a double mobility prosthetic engaging subassembly, and at the opposite end, a handle which facilitates activation of the drive train and movement of the subassembly. The inserter enables easy orientation of a double mobility prosthesis attached to its end. This is important because precise control of the prosthetic is critical in implantation of the prosthetic in a patient.

The subassembly comprises a series of components, a domed nose, an impaction plate and a grasping plate having a plurality of legs with grasping hook ends extending from its central region. The grasping hook ends work in concert to grip the outside perimeter of the prosthetic cup.

An objective of the invention is to provide a novel design by which the double mobility cup prosthesis is manipulated and inserted into the body with minimum stresses imparted to the cup. The present invention provides an inserter by which potential damage caused by the implantation procedure is minimized to the implant, thereby reducing the possibility that the cup is damaged during the implantation process.

A further objective is to provide an inserter that can be "easily cleaned" by quick and modular disassembly which enables access to all surfaces that can be cleaned. The reduction in the number of small radius internal corners, crevices and small gaps and the absence of blind holes also aids in the sterilization of the instrument.

DETAILED DESCRIPTION OF THE PREFERRED EMBODIMENT(S)

Referring now to FIGS. 1A-9, an acetabular inserter 10 is provided to aid the surgeon in controlling installation of an acetabular cup prosthesis 12. The inserter 10 has a housing 14 which encloses a drive train 16 having, at a distal end, a prosthesis engaging subassembly 18, and at the proximal end, a handle 20 which facilitates moving of the drive train by the operator. The housing 14 may be C-shaped, as shown, in order to minimize invasiveness of the surgery by better clearing anatomical structures and tissue.

Figure 2:
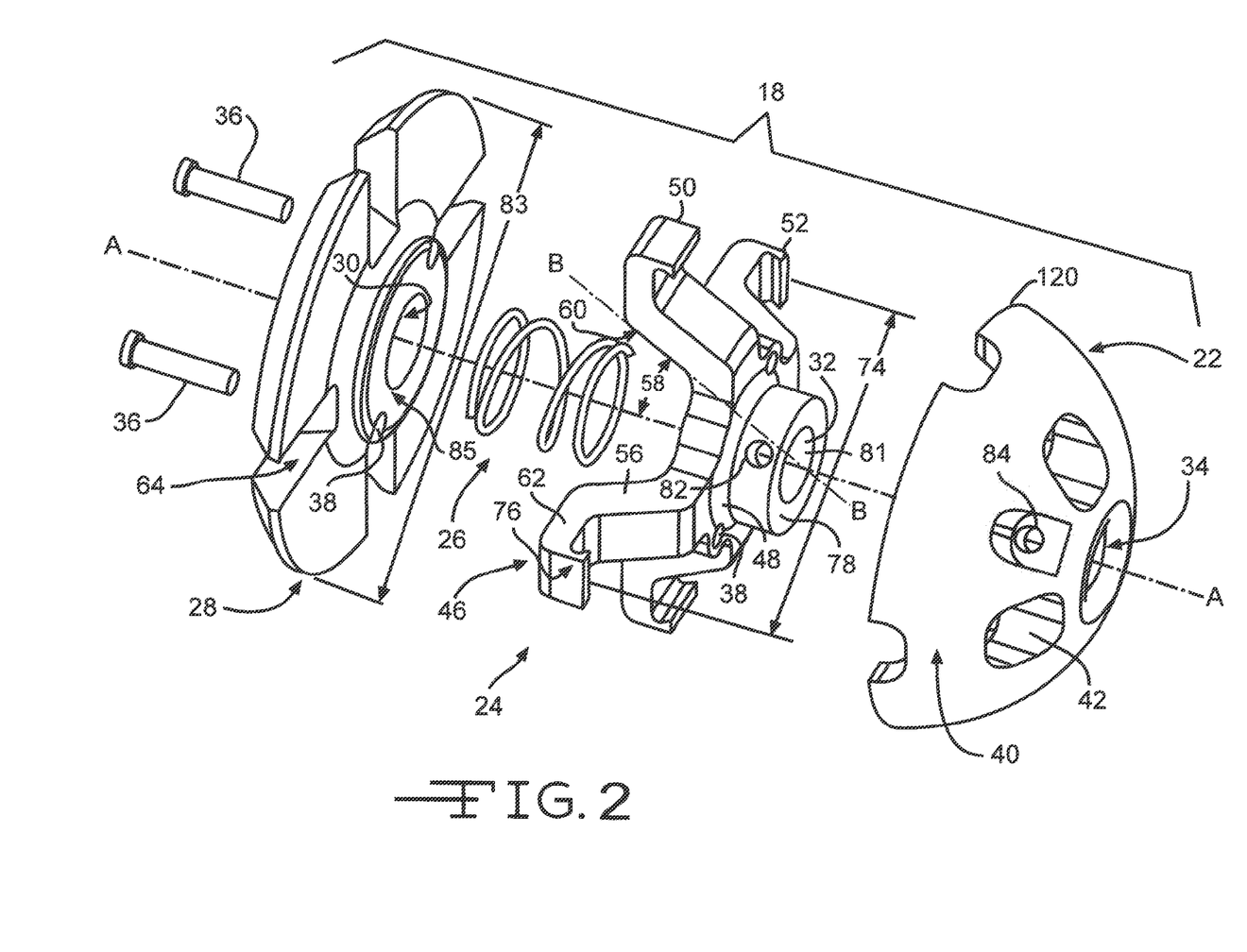
FIG. 2 shows an exploded view of the components that comprise the prosthesis engaging subassembly.
Figure 3:
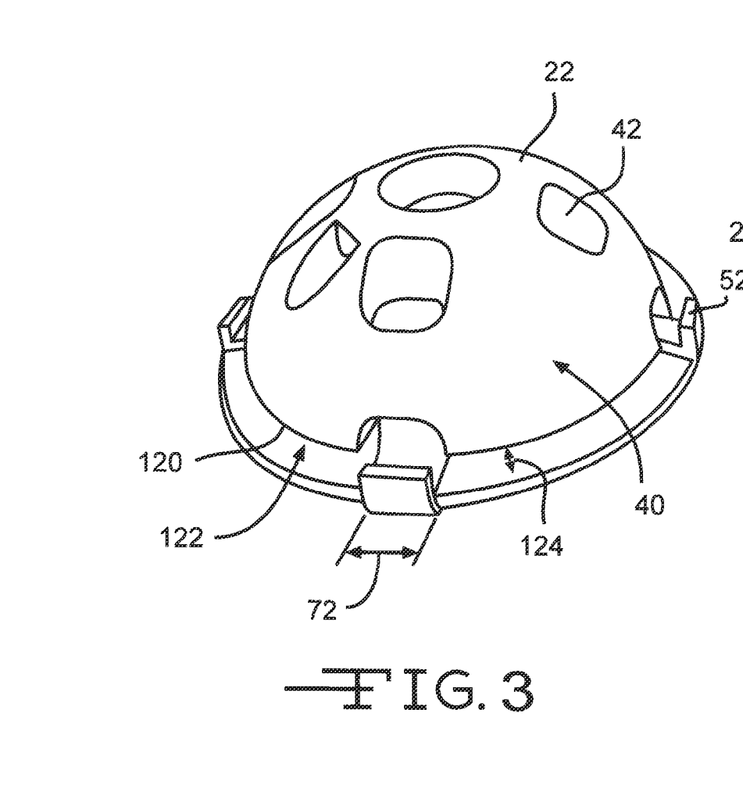
FIG. 3 shows a perspective view of the assembled prosthesis engaging subassembly.

The prosthesis engaging subassembly 18, as illustrated in FIGS. 2 and 3, comprises a nose 22, a grasping plate 24, a spring 26, and an impaction plate 28 that are in direct communication with each other. The grasping plate 24 is positioned between the impaction plate 28 and the nose 22. The spring 26 is further positioned between the impaction plate 28 and the grasping plate 24 of the subassembly 18. Respective axial through-bores 30, 32, 34 extend parallel longitudinal axis A-A, through the center of each of the components of the prosthesis engaging subassembly 18. A series of pins 36 positioned through respective pin openings 38, align and support the components of the subassembly 18 together.

The nose 22 is positioned at the distal end of the prosthesis engaging subassembly 18. The nose 22 is designed with a curved, domed outer surface 40 that is designed to be positioned within an inside cavity 43 of the double mobility acetabular cup prosthesis 12. As shown in FIG. 2, the outside surface 40 has a plurality of openings 42 which penetrate therethrough. These openings 42 are designed to minimize the transfer of mechanical stresses from the body of the inserter 10 to the prosthesis 12 during implantation. While the nose 22 is designed to be positioned within the inside cavity 43 of the prosthetic cup 12, it should be noted however, that it is not desirable for the outside surface 40 of the nose 22 to contact the inside surface 44 of the cup implant 12. Such contact between the nose 22 and the inside surface 44 of the cup implant 12, could result in transfer of the mechanical insertion forces throughout the structure of the implant 12, resulting in damage to the implant 12. For example, when the cup 12 is impacted within the body, the mechanical stress of the impacting force could be transferred to the inside surface 44 of the implant 12, thereby potentially cracking or weakening the structure of the cup implant 12. Furthermore, contact between the outside surface 40 of the nose 22 and inside surface 44 of the implant 12 could result in a marred surface affecting the mobility of the resulting hip replacement implant.

As the name implies, the grasping plate 24 is designed to grasp and hold the double mobility prosthesis implant 12. The grasping plate 24 comprises a plurality of legs 46 that extend from a central region 48 of the plate 24. A hook 50 is formed at the distal end of each of the respective legs 46 along the periphery of the plate 24. As will be described in more detail, the hooks 50 are designed with a lip 52 that engages a groove 54 (FIGS. 5 and 6) that resides along the outside edge of the perimeter of the cup implant 12. It is this hook 50 and groove 54 feature that grasps and secures the implant 12 to the distal end of the inserter 10.

Furthermore, each of the legs 46 is preferably angled such that they extend in a proximal direction towards the handle 20 and away from the central region 48 of the plate 24. As illustrated in FIG. 2, each leg 46 comprises a first leg portion 56 that extends outwardly and downwardly from the central region 48 of the grasping plate 24. In a preferred embodiment, each leg 46 is angled at a first leg portion angle 58 that ranges from about 20° to about 60°. The first leg portion angle 58 is defined as the angle between the intersection of longitudinal axis A-A and an imaginary line B-B that is tangent to an underside surface 60 of the first leg portion 56. A second leg portion 62 preferably extends from the distal end of the first leg portion 56. The second leg portion 62 comprises the bottom portion of the hook end 50.

In a preferred embodiment, the second portion 62 is substantially perpendicular to the longitudinal axis A-A. When the grasping plate 24 is assembled in the prosthesis engaging subassembly 18, it is preferred that the second portion 62 of the leg 46 resides within an inlet opening 64 of the impaction plate 28. It is further preferred that a backside surface 66 of the second leg portion 62 is about flush with a proximal surface 68 of the impaction plate 28.

The length 70 of the legs 46 may range from about 5 cm to about 20 cm depending on the design and diameter of the impaction plate 28. It is also preferred that the width 72 of the hook end 50 may range from about 1 cm to about 5 cm. It is important that each leg 46 of the grasping plate 24 is designed such that its length 70 does not extend past the outer perimeter of the impaction plate 28. This design feature minimizes potential contact of the leg 46, particularly the hook end 50, with body tissue as the legs 46 are drawn in a proximal direction, through their respective inlet openings 64. Such contact between the hook end 50 and body tissue could result in the tearing of tissue and potential damage to the inserter itself as the prosthetic cup 12 is impacted into position within the body.

It is further preferred that a grasping plate diameter 74 range from about 5 cm to about 20 cm. The diameter 74 of the grasping plate 24 is defined as the distance between opposing hook surfaces 76. The diameter 74 of the grasping plate 24 is illustrated in FIG. 2. It is preferred that the diameter 74 of the grasping plate 24, approximates the diameter of the impaction plate 28.

In a further embodiment, the grasping plate 24 comprises a standoff 78 that extends from a distal surface 80 of the grasping plate 24. The standoff 78 is further positioned such that it resides about the central region 48 of the grasping plate 24. The standoff 78 has a curved shaped with a diameter that ranges from about 2 cm to about 10 cm and a height that ranges from about 1 cm to about 5 cm. The standoff 78 further comprises a standoff wall 81 that surrounds a standoff through-bore 32. The standoff 78 is designed to be positioned within a receiving end of the underside of the nose 22 and serves to secure the nose 22 to the grasping plate 24. As illustrated, the standoff 78 may comprise an opening 82 through the wall 81 of the standoff 78 such that when the standoff 78 is engaged within the receiving end of the nose 22, a fastener (not shown), such as a pin or screw, may be positioned through a corresponding opening 84 of the nose, thus securing the grasping plate 24 therebetween.

The impaction plate 28 is positioned proximal of the nose 22 and grasping plate 24. The impaction plate 28 serves as a back stop for the prosthesis engaging subassembly 18. As such, the impaction plate 28 remains in a fixed position at the distal end of the inserter 10 and at the proximal end of the prosthesis engaging subassembly 18. The impaction plate 28 is designed with a curved shape and more preferably, of a circular shape. In a preferred embodiment, the impaction plate 28 has a diameter that approximates the diameter of the prosthetic cup implant 12. As such, a diameter 83 of the impaction plate 28 may range from about 5 cm to about 20 cm depending of the diameter of the cup implant 12. The plurality of inlet openings 64 each extend through the outer perimeter of the plate 28 to a region about the axial through-bore 30. The inlet openings 64 are designed such that the backside surface 66 of the second leg portion 62 is about flush with the proximal surface 68 of the impaction plate 28. The inlet openings 64 are further designed such that a portion of the legs 46 and hook ends 50 of the grasping plate 24 pass therethrough without obstruction.

When activated by the drive train 16 of the inserter 10, the grasping plate 24 moves in a proximal direction within the prosthesis engaging subassembly 18. As the grasping plate 24 moves proximally, the combination of the grasping plate 24 and nose 22, compresses the spring 26 against a distal surface 85 of the impaction plate 28. As the grasping plate 28 continues to move in a proximal direction, the legs 46 of the grasping plate 24 pass through their respective inlet openings 64 of the impaction plate 28, thus providing room for the grasping plate 24 to move. As the grasping plate 24 moves in a proximal direction, the hook ends 50 of the legs 46 move along with the legs 46 in a proximal direction securing the mobility acetabular cup prosthesis 12 to the distal end of the inserter 10.

Figure 1A:
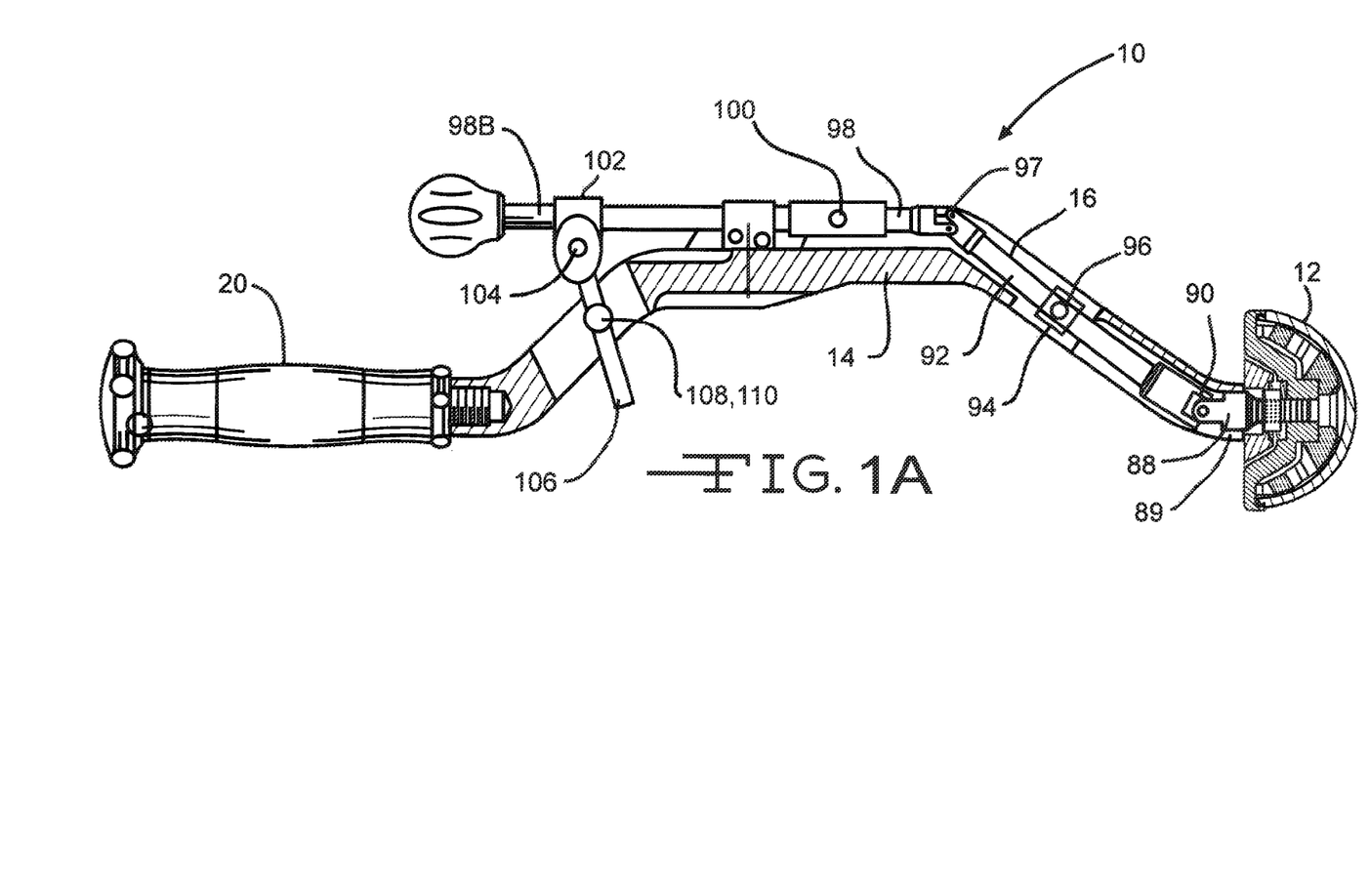
FIG. 1A is a cross-sectional side view of the inserter of the present invention.
Figure 1B:
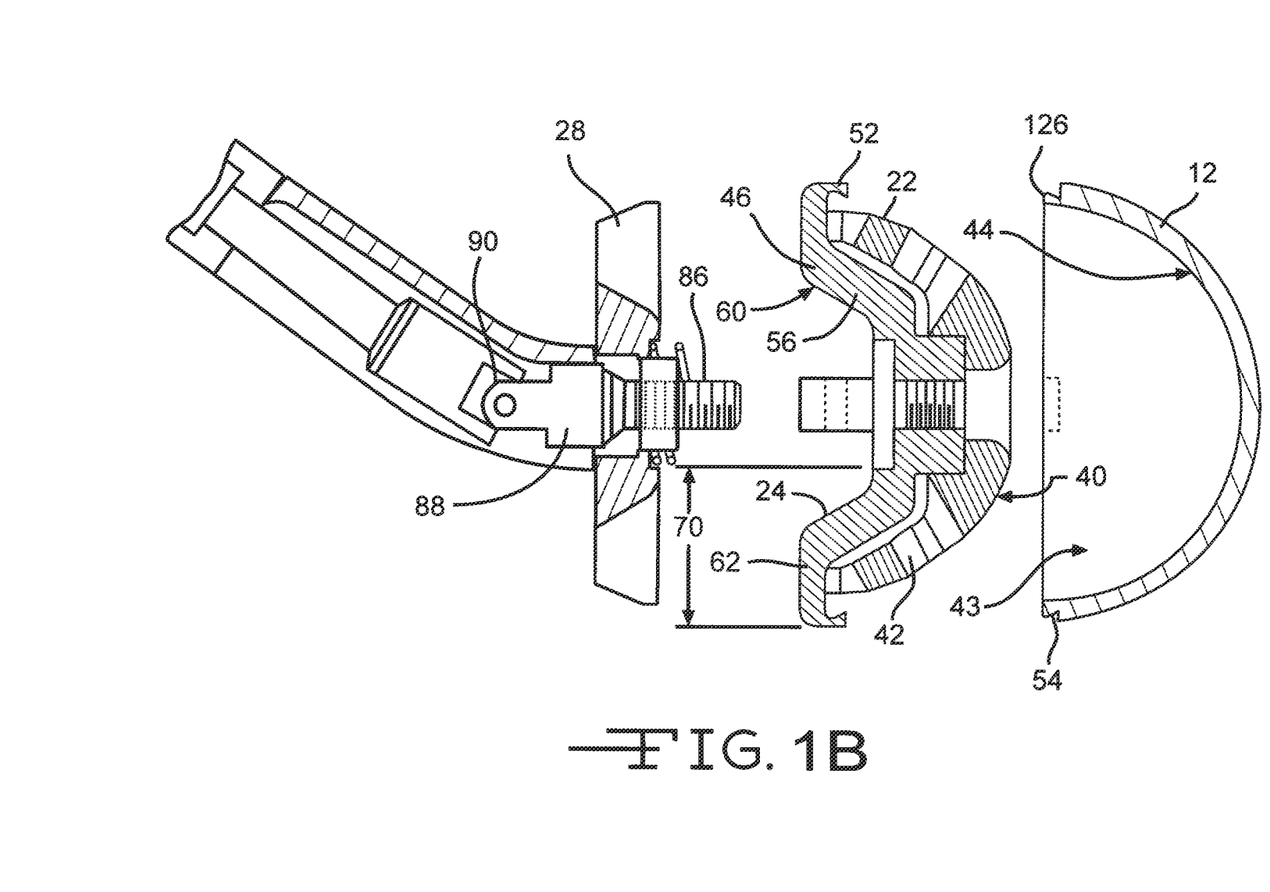
FIG. 1B is a magnified cross-sectional side view of the components that comprise the double mobility prosthesis engaging subassembly.
Figure 8:
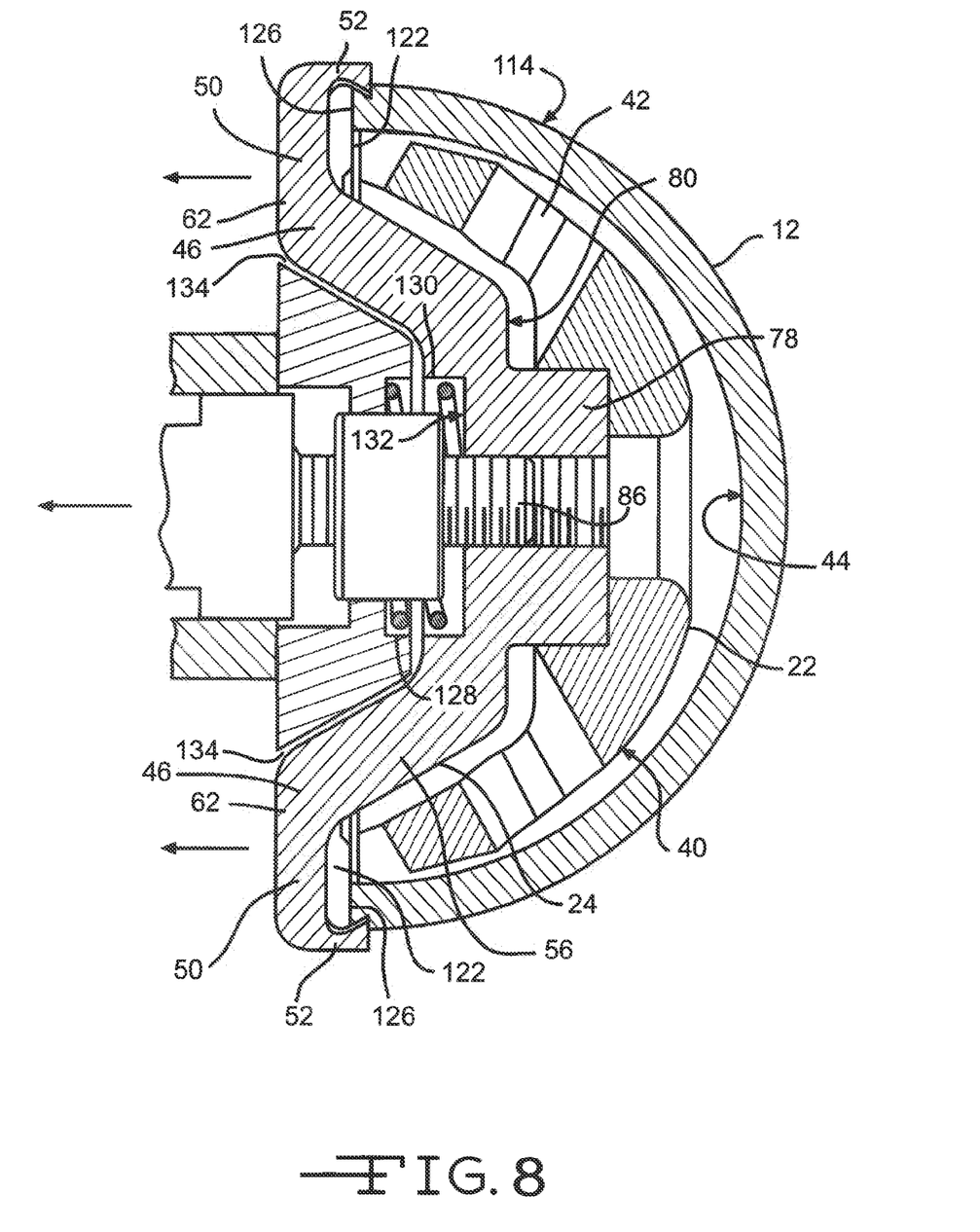
FIG. 8 illustrates a cross-sectional view of a cup implant attached to the distal end of the inserter.
Figure 9:
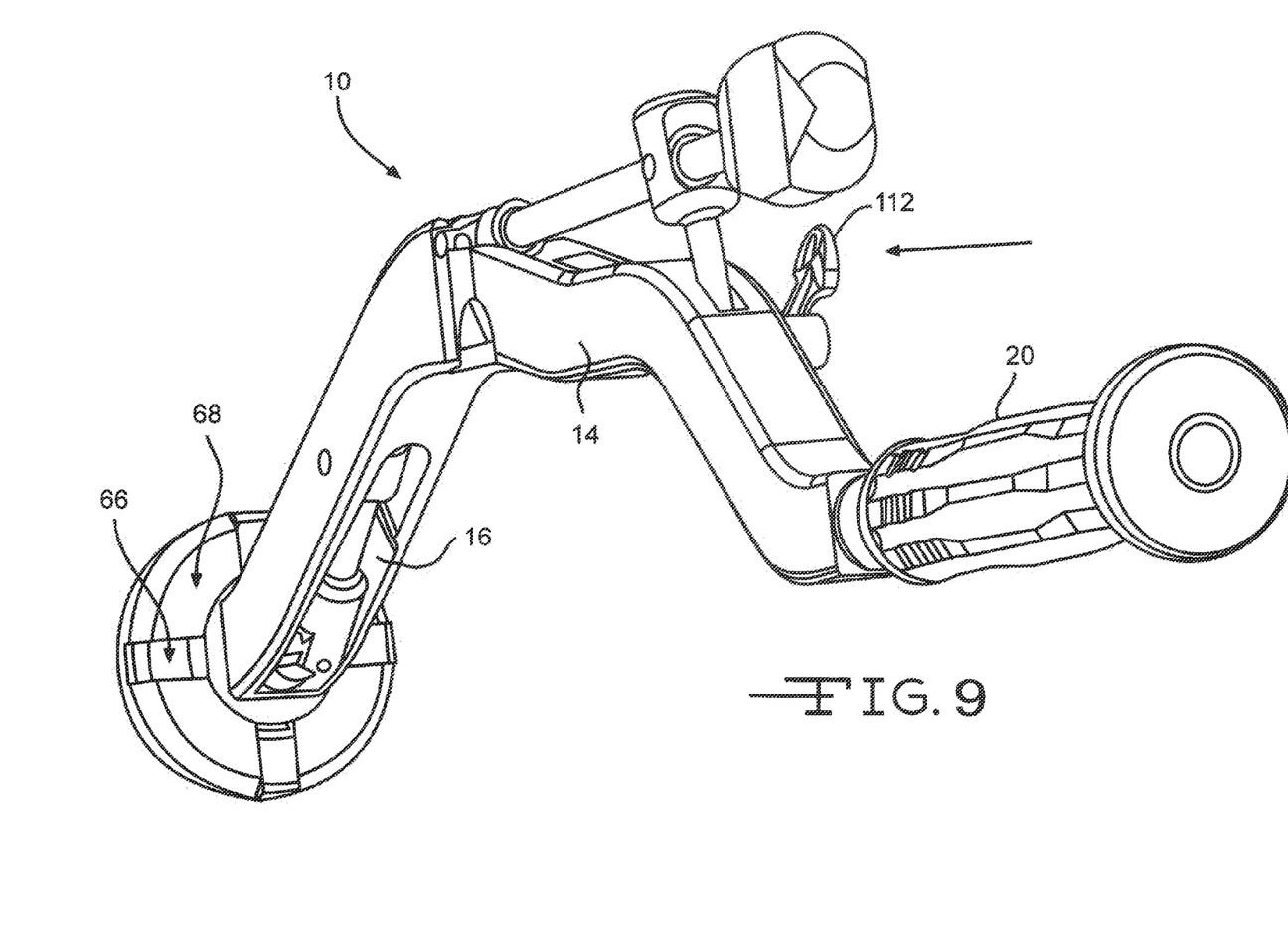
FIG. 9 shows a perspective view from the proximal end of the inserter of the invention.

In a preferred embodiment, the prosthesis engaging subassembly 18 is connected to the distal end of the housing 14. A cylindrical rod 86, which is connected to a cylindrical piston 88, slides through the axial bore 30 that penetrates through the impaction plate 28 and into the grasping plate 24, respectively. The cylindrical rod 86 is preferably threaded. The cylindrical rod 86 is threaded into a corresponding threaded groove of the axial through-bore 32 of the grasping plate 24 securing it in place as shown in FIGS. 1A, and 8-9. In a preferred embodiment, the grasping plate 24 and impaction plate 28 may be made of a metal material such as stainless steel, MP35N, aluminum or the like.

With respect to the drive train 16, the piston 88 is connected by way of a first U-joint 90 to a lever 92 which slides in a pivoting sleeve 94 fixed to the housing 14 via a pivot 96. The lever 92 is connected via a second U-joint 97 to a second pivoting lever 98 which is fixed to pivot in a catch 101 (FIG. 7) on a pivot pin 100. The catch 101 is essentially a divot or a seat cut into the housing 14, against which the pivot pin 100 of the lever 98 is captured when a slide is slid over the pin 100 when engaged against the seat.

A slideable sleeve 102 slides over the lever 98 and has a trunnion 104 to which a rod 106 is pivotally attached. The rod 106 passes through a one-way catch 108 in the housing 14. The one-way catch 108 can be a captured split wedge sleeve 110 having an inner diameter that just matches the outer diameter of the rod 106. The split wedge sleeve 110 is captured in a recess having a matching conical surface that surrounds the sleeve so as to allow the rod 106 to slide into the housing 14, but to prevent the rod 106 from sliding out of the housing 14 unless an unlock lever 112 (FIG. 9) is activated. Manipulation of the lever lifts the sleeve 102 out of engagement with the conical surface into an unlocked position to permit the rod 106 to back out of the housing 14. Any number of alternative one-way lock devices may be used, however, the selection of which being within the skill of a person of ordinary skill in this field. For greater detail regarding the drive train 16 supported by the housing 14, reference is made to U.S. Pat. No. 7,682,363 to Burgi et al., which is assigned to the assignee of the present invention and incorporated herein by reference.

Figure 5:
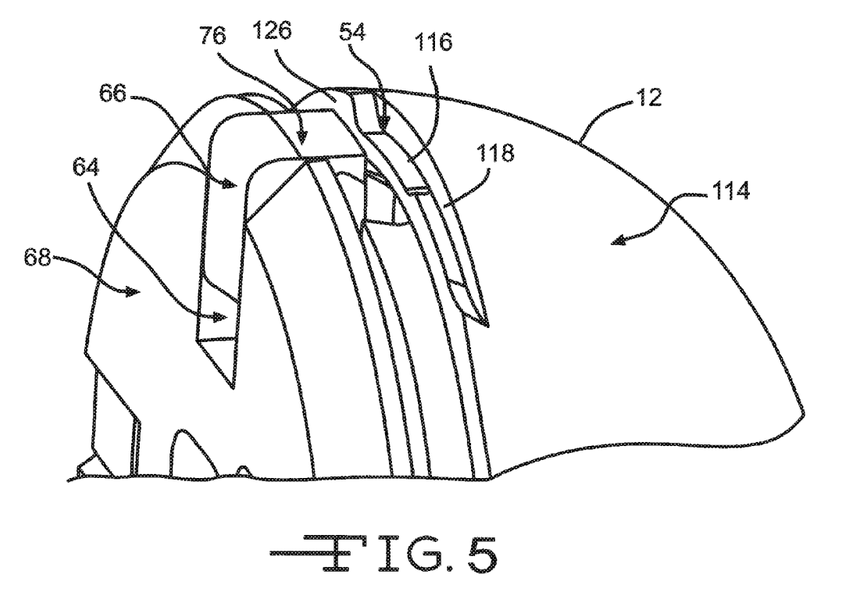
FIG. 5 shows a perspective view of an embodiment of a groove and hook alignment, of the cup implant.
Figure 6:
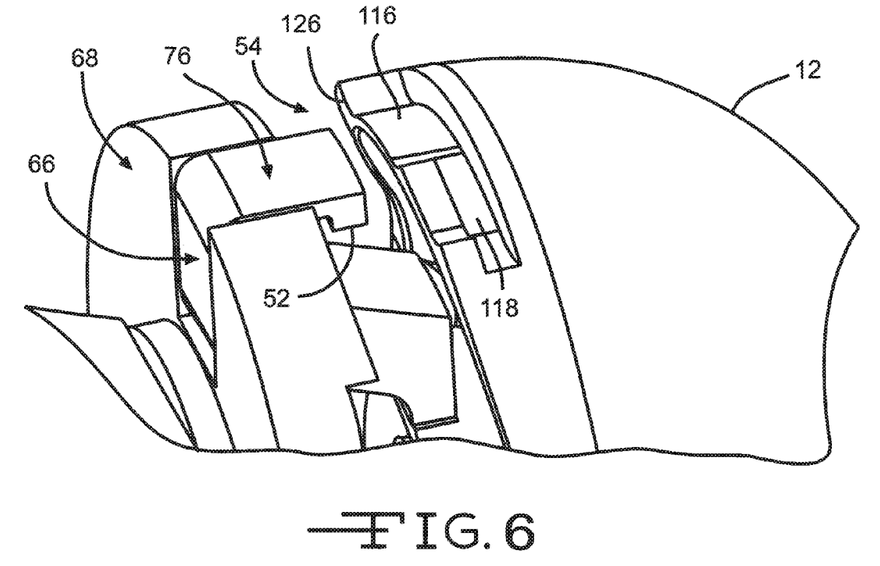
FIG. 6 illustrates a perspective view of an alternate embodiment of a groove of the cup implant.
Figure 7:
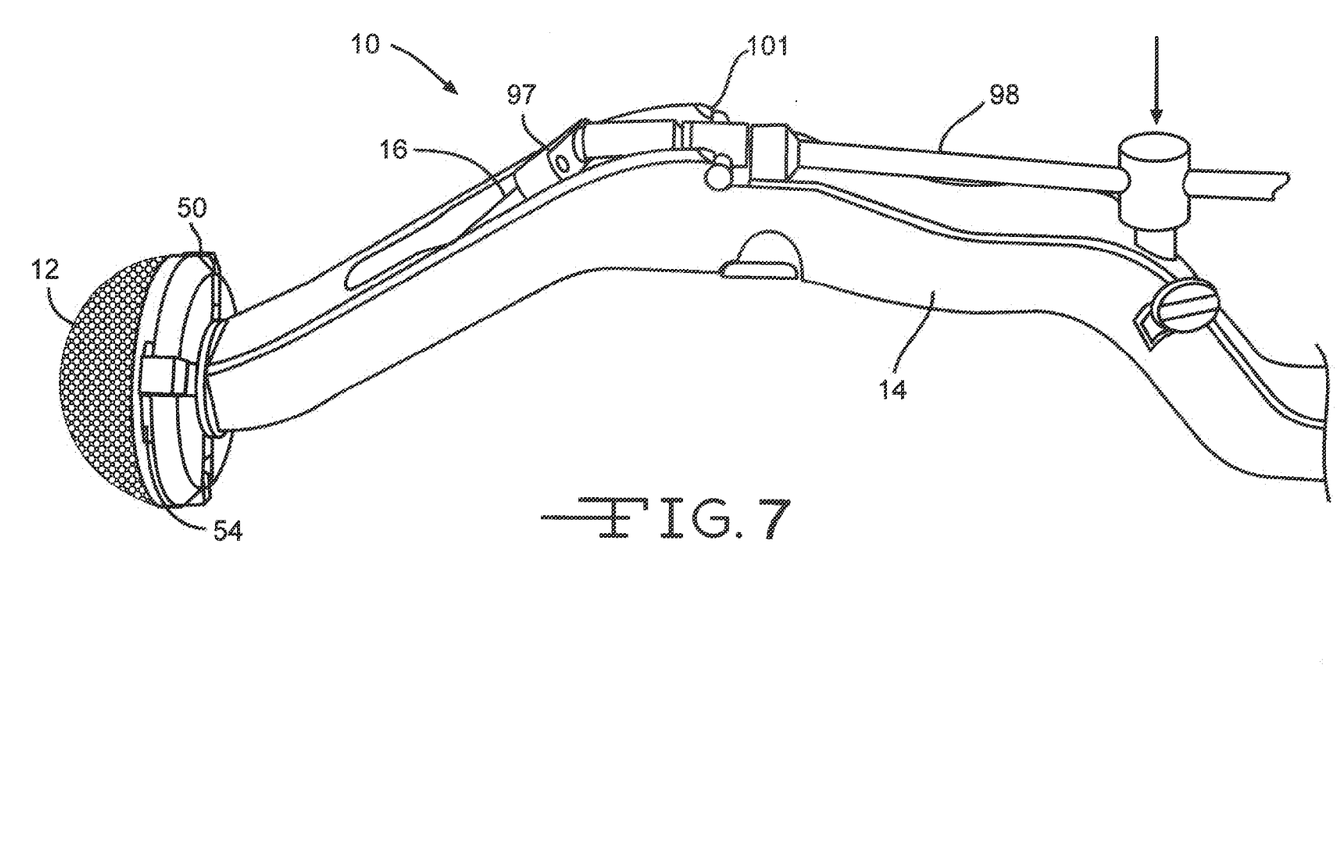
FIG. 7 shows a perspective view with a cup implant attached to the inserter of the invention.

As previously mentioned, the legs 46 of the grasping plate 24 preferably comprise a hook end 50. These hook ends 50 are designed to slide over and engage the groove 54 of the cup implant 12. As shown in the embodiment of FIGS. 5 and 6, the groove 54 is preferably positioned within an outer surface 114 at the proximal end of the implant 12 along its outer perimeter. The groove 54 is further designed with a recessed portion 116 that allows the hook end 50 to slide over the outer perimeter of the implant 12. Once the cup implant 12 is positioned over the distal end of the nose 22, the implant 12 is then rotated in either a clockwise or counter clockwise orientation, from about 5° to about 15°, such that the lip 52 of the hook end 50 of the grasping plate 24 slides within a groove track 118 of the implant 12. Once the lip 52 of the hook end 50 is slid within the groove track 118, the lip 52 is secured by the interference fit of the track 118. This initial engagement of the hook end 50 is illustrated in the embodiments shown in FIGS. 5 and 6.

As shown in FIG. 5, the groove 54 may be designed with a narrow width and a tapered depth. Alternatively, as shown in FIG. 6, the groove 54 may have a wider width than the embodiment shown in FIG. 5. Furthermore, the groove 54 as illustrated in FIG. 6 may have a raised portion which provides additional security to the hook 50 and groove 54 engagement. In either case, the groove 54 is designed such that the hook end 50 latches onto and secures the implant 12 to the prosthesis engaging subassembly 18.

In a preferred embodiment, a base 120 of the domed nose 22 has a diameter that is smaller than the diameter 83 of the impaction plate 28. This mismatch in diameters between the base 120 of the nose 22 and the diameter 83 of the impaction plate 28 creates an impaction strike surface 122 (FIG. 3). This strike surface 122 of the impaction plate 28 extends circumferentially around the base 120 of the nose 22. In a preferred embodiment, the strike surface 122 has a strike surface width 124 that ranges from about 1 cm to about 5 cm. When the cup implant 12 is attached to the prosthesis engaging subassembly 18, this strike surface 122 preferably contacts a rim 126 of the cup implant 12. Therefore, when an impaction strike is delivered to the proximal end of the housing 14 of the inserter 10, the force of the blow is preferably transferred from the strike surface 122 of the impaction plate 28 to the rim 126 of the prosthetic cup 12, thereby minimizing the potential of transferring the impaction forces throughout the structure of the implant 12. Having the cup implant 12 connected to the distal end of inserter 10 by the hook ends 50 along the outside perimeter of the cup 12 provides an offset that minimizes direct transfer of the insertion force. This structure further minimizes the possibility that the cup implant 12 is damaged during implantation.

The nose 22 is sized to be positioned within a multitude of different double mobility implants 12 having different diameters and depths. As such, the diameter of the base 120 of the dome nose 22 may range from about 2 cm to about 20 cm. The depth of the nose 22 may range from about 2 cm to about 10 cm.

When activated, the cylindrical rod 86 slides proximally towards the distal end of the housing 14. The rod 86 pulls the attached grasping plate 24 and nose 22 combination proximally towards the impaction plate 28 of the subassembly 18. The spring 26, positioned between a first recessed portion 128 of the distal surface 85 of the impaction plate 28 and a second recessed portion 130 of a proximal surface 132 of the grasping plate 24, provides a resistive mechanical force between the two plates 24, 28. In addition, the spring 26 provides a space 134 between the grasping plate 24 and the impaction plate 28 (FIG. 8).

It is this space 134 between the impaction plate 28 and the grasping plate 24, provided by the spring 26, that further minimizes the transfer of mechanical impaction forces to the structure of the cup implant 12. In other words, the gap 134 between the impaction plate 28 and the grasping plate 24 holding the cup implant 12 in place minimizes transfer of the impaction forces from the impaction plate 28 through the prosthesis engaging subassembly 18 to the nose 22. Instead, the impaction force is preferably concentrated at the rim surface 126 of the cup implant 12. Therefore, the magnitude of the impaction force being delivered throughout the remaining structure of the implant cup 12 is minimized and the potential of resulting implant cup 12 damage is decreased.

Figure 4:
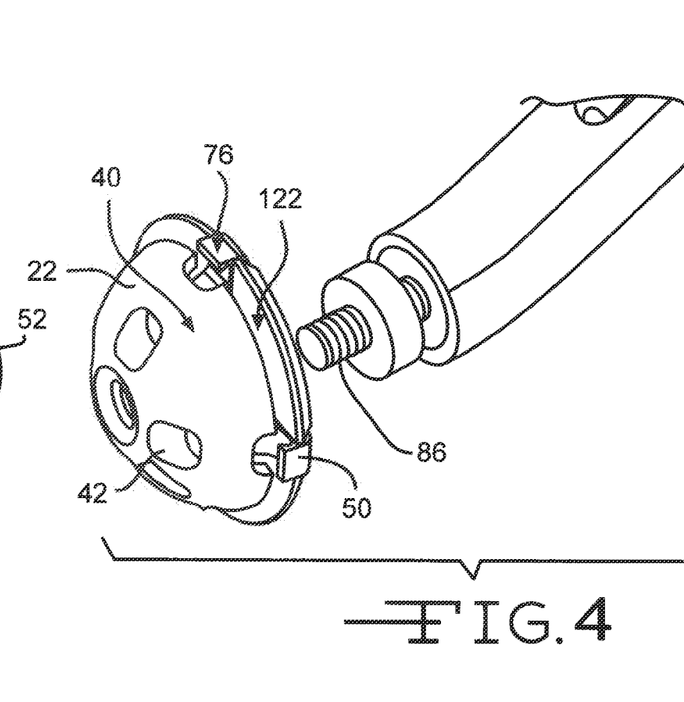
FIG. 4 illustrates a perspective view of the attachment of the prosthesis engaging subassembly to the distal end of the inserter.

Referring now to FIG. 4, in operation, first the prosthesis engaging subassembly 18 is threaded onto the threaded cylindrical rod 86. The prosthetic cup 12 is then placed on the distal end of the subassembly 18. The prosthetic cup 12 is secured to the prosthesis engaging subassembly 18 such that the hook ends 50 are placed within the track of the groove or grooves 54 that reside along the outer perimeter of the cup 12. Once the hook 50 is initially placed in the groove 54 of the cup 12, the prosthetic cup 12 is then rotated to secure the lip 52 of the hook 50 further into the groove track 118. It should be noted that although the inserter 10 comprising the drive train 16 as previously described is preferred, it is contemplated that the prosthesis engaging subassembly 18 of the present invention may be utilized with any non limiting orthopedic inserter device. Furthermore, that the prosthesis engaging subassembly 18 of the present invention may also be attached to a multitude of non-limiting drive train designs.

The operator may rotate the handle 20 about its axis to turn the drive train 16 in order to orient the prosthesis in what he believes to be a correct or an initial position. Then, the proximal end 98B of the lever 98 is urged downwardly toward the housing 14. Such downward movement acts through the drive train 16 to draw the piston 88 into the housing 14, and thus to cause the grasping plate 24 and attached nose 22 to move proximally against the spring 26 towards the impaction plate 28. The lip 52 of the hook ends 50 of the grasping plate 24 are thus drawn proximally within the groove track 118 of the cup prosthesis 12 pulling the rim 126 of the prosthetic 12 against the strike surface 122 of the impaction plate 28.

The operator may use the one way locking mechanism 106 to lock the lever 98 in a position so as to lock the rim 126 of the cup implant 12 against the impaction plate 28, thus enabling the surgeon to pre-set and lock the position of the prosthesis 12 prior to the installation thereof.

Once correctly positioned within the body, impaction forces are delivered to the proximal end of the inserter 10. These impaction forces are intended to drive the prosthetic cup implant 12 to the desired location within the body. Once the cup implant 12 is securely in place, the tension between the lip 52 of the hook end 50 and the groove track 118 is released. The release button 112 (FIG. 9) is depressed allowing the one way locking mechanism 106 to move in a reverse direction, thereby relieving the applied pressure of the hooks 50 to the prosthetic cup 12. The operator may then rotate the handle 20 in a direction opposite the direction the prosthetic cup 12 was initially rotated in attaching it to the subassembly 18. Once the hooks 50 are aligned with the peripheral recesses 116 of the prosthetic cup 12, the inserter 10 is removed from the body leaving the double mobility prosthetic cup 12 behind within the body.

The inserter 10 is designed to be disassembled for cleaning by simply sliding the slide back so as to release the pivot 101 and then lifting the drive train 16 out of the housing, but allow it to remain pivotally connected at pivot 96. As the drive train 16 is pivoted, the piston 88 is drawn out of the housing cavity 89. To reassemble after cleaning, the piston 88 is reinserted into the housing cavity 89 and the drive train 16 is rotated back into position, with the one way locking mechanism entering its receiver and the pivot 96 again entering into the catch 101. The slide is then slid over the pivot 96 and the inserter 10 is again ready for use.

The present invention can be packaged in a kit offering a variety of double mobility prosthetic implants 12 of different sizes and diameters. The inserter 10 and assorted double mobility implants 12 and subassemblies 18 can be packaged in a case with recesses which conveniently holds the components in a convenient, easy to access manner.

The attached drawings represent, by way of example, different embodiments of the subject of the invention. Multiple variations and modifications are possible in the embodiments of the invention described here. Although certain illustrative embodiments of the invention have been shown and described here, a wide range of modifications, changes, and substitutions is contemplated in the foregoing disclosure. In some instances, some features of the present invention may be employed without a corresponding use of the other features. Accordingly, it is appropriate that the foregoing description be construed broadly and understood as being given by way of illustration and example only, the spirit and scope of the invention being limited only by the appended claims.

What is claimed is:

1. An inserter system for aiding a surgeon in controlling the installation of a prosthesis cup, the inserter system comprising:
  a) a prosthesis engaging assembly, comprising:
    i) an impaction plate comprising an impactor plate central region having a through bore aligned along a longitudinal axis, wherein a plurality of inlets extend from a perimeter of the impaction plate toward, but ending spaced from the impaction plate through bore;
    ii) a grasping plate positioned along the longitudinal axis distal the impaction plate, wherein the grasping plate is of a unitary, one-piece construction comprising a grasping plate central region rigidly supporting at least two spaced apart and outwardly extending grasping legs, wherein the grasping plate central region surrounds a grasping plate bore in co-axial alignment with the impactor plate through bore, and wherein each of the grasping legs extends from a rigid connection at the grasping plate central region to a distal grasping leg portion, wherein one of the distal grasping leg portions is aligned with a respective one of the impaction plate inlets; and
    iii) a spring disposed between the impaction plate and the grasping plate;
  b) an inserter, comprising:
    i) a housing comprising a proximal housing end and a distal housing end supporting the impaction plate; and
    ii) a drive train at least partially housed inside the housing, the drive train extending through the impaction plate bore and being releasably connectable to the grasping plate at the grasping plate bore; and
  c) a prosthesis cup comprising at least two spaced apart outer grooves adjacent to a perimeter of a rim of the cup;
  d) wherein the prosthesis cup is positionable adjacent to the grasping plate and then the prosthesis cup and the at least two grasping legs rigidly connected to the grasping plate are relatively rotatable with respect to the longitudinal axis of the grasping plate to thereby cause a distal grasping leg portion of one of the grasping legs to rigidly engage with a respective one of the outer grooves of the cup; and
  e) wherein the drive train is then actuatable along the impaction plate bore to thereby draw the grasping plate including the rigid grasping legs engaging the cup in a proximal direction against a bias of the spring from a first position spaced from the impaction plate to a second position contacting the impaction plate with at least a portion of the rigid grasping legs received in respective ones of the impaction plate inlets so that the housing, impaction plate, grasping plate and cup are in rigid contact alignment.

2. The inserter system of claim 1 wherein the distal grasping leg portion is a distal hook end that is positionable within an outer groove of the prosthesis cup adjacent to the perimeter of the cup rim.

3. The inserter system of claim 2 wherein a distal piston of the drive train is extendable through the impaction plate through bore and then releasably connectable to the grasping plate at the grasping plate bore and wherein actuation of the drive train draws the piston in a proximal direction towards the housing, to thereby draw the distal hook ends of the at least two grasping legs and the prosthesis cup in a proximal direction to thereby position the prosthesis cup in a contact relationship against the impaction plate.

4. The inserter system of claim 3 wherein with a prosthesis cup in the contact relationship against the impaction plate, the rim of the prosthesis cup contacts a strike Surface of the impaction plate.

5. The inserter system of claim 2 wherein the hook ends of the grasping legs are rotatably positionable within respective ones of the grooves through relative rotation movement of from 5° to 15° of the hook ends with respect to the cup.

6. The inserter system of claim 1 wherein each of the at least two grasping legs comprise a first leg portion and a second leg portion, and wherein the first leg portion forms an angle from 20° to 60° with respect to the longitudinal axis and wherein the second leg portion is distal the first leg portion.

7. The inserter system of claim 1 wherein a dome-shaped nose is secured to a distal standoff portion of the grasping plate.

8. The inserter system of claim 7 wherein a space is provided between an outer surface of the nose and an inner surface of the prosthesis cup.

9. The inserter system of claim 1 wherein the drive train of the inserter further comprises:
  a) a first lever comprising a first lever proximal end spaced apart from a first lever distal end located adjacent to the distal housing end;
  b) a second lever comprising a second lever proximal end located adjacent to the proximal housing end and spaced apart from a second lever distal end;
  c) a piston comprising a piston proximal end space apart from a piston distal end releasably connected to the grasping plate, wherein the second lever distal end is in a universal joint relationship with the first lever proximal end, and wherein the first lever distal end is in a universal joint relationship with the piston proximal end and the piston distal end extends through the longitudinally extending bore of the impaction plate of the prosthesis engaging assembly;
  d) a first sleeve pivotably connected to the housing, wherein the first lever is in a slidable relationship with a first opening in the first sleeve disposed at an intermediate location between the first lever proximal end and the first lever distal end; and
  e) wherein the second lever proximal, end is manipulable from a first position spaced from the housing to a second position spaced closer to the housing than the first spaced position to cause the second lever to pivot with respect to the housing and thereby move the second lever distal end away from the distal housing end and to further cause the first lever to move away from the distal housing end along the first opening in the first sleeve as the first sleeve pivots on the housing to thereby cause the piston to move along the longitudinal bore in the impaction plate with the prothesis cup engaged with grasping plate connected to the piston distal end moving from the first position spaced from the impaction plate to the second position closer to the impaction plate than the first position.

10. The inserter system of claim 1 wherein the housing is C-shaped

11. The inserter system of claim 1 wherein a first outer diameter of the grasping plate approximates a second. outer diameter of the impaction plate.

12. A surgical kit, which comprises:
  a) at least one inserter according to claim 1;
  b) at least one prosthesis cup; and
  c) a case for organizing components of the kit including the at least one inserter and the at least one prosthesis cup.

13. The inserter system of claim 1 wherein the prosthetic cup implant is a double mobility prosthetic cup implant.

14. An inserter system for aiding a surgeon in controlling the installation of a prosthesis cup, the inserter system comprising:
  a) a prosthesis engaging assembly, comprising:
    i) an impaction plate comprising an impactor plate central region having a through bore aligned along a longitudinal axis, wherein a plurality of inlets extend from a perimeter of the impaction plate toward, but ending spaced from the impaction plate through bore;
    ii) a grasping plate positioned along the longitudinal axis distal the impaction plate, wherein the grasping plate is of a unitary, one-piece construction comprising a grasping plate central region rigidly supporting at least two spaced apart and outwardly extending grasping legs, wherein the grasping plate central region surrounds a grasping plate bore in co-axial alignment with the impactor plate through bore, and wherein each of the grasping legs extends from a rigid connection at the grasping plate central region to a distal grasping leg portion, wherein one of the distal grasping leg portions is aligned with a respective one of the impaction plate inlets;
    iii) a dome-shaped nose secured to a distal standoff portion of the grasping plate; and
    iv) a spring disposed between the impaction plate and the grasping plate;
  b) an inserter, comprising:
    i) a housing comprising a proximal housing end and a distal housing end supporting the impaction plate; and
    ii) a drive train at least partially housed inside the housing, the drive train extending through the impaction plate bore and being releasably connectable to the grasping plate at the grasping plate bore; and
  c) a prosthesis cup comprising at least two spaced apart outer grooves adjacent to a perimeter rim of the cup;
  d) wherein the prosthesis cup is positionable adjacent to the grasping plate and then the prosthesis cup and the at least two grasping legs rigidly connected to the grasping plate are relatively rotatable with respect to the longitudinal axis of the grasping plate to thereby cause a distal grasping leg portion of one of the grasping legs to rigidly engage with a respective one of the outer grooves of the cup; and
  e) wherein the drive train is actuatable along the impaction plate bore to thereby draw the dome-shaped nose and the grasping plate including the rigid grasping legs engaging the cup in a proximal direction against a bias of the spring from a first position spaced from the impaction plate to a second position contacting the impaction plate with the rigid grasping legs received in respective ones of the impaction plate inlets so that the housing, impaction plate, grasping plate and cup are in rigid contact alignment.

15. The inserter system of claim 14 wherein with a prosthesis cup in the contact relationship against the impaction plate, the rim of the prosthesis cup contacts a strike surface of the impaction plate.

16. The inserter system of claim 15 wherein with the prosthesis cup in the second position having the rim of the prosthesis cup contacts a strike surface of the impaction plate, the cup does not contact the dome-shaped nose.

17. The inserter system of claim 14 wherein the distal grasping leg portion is a distal hook end that is positionable within an outer groove of the prosthesis cup adjacent to the perimeter of the cup rim.

18. The inserter system of claim 17 wherein the hook ends of the grasping legs are rotatably positionable within respective ones of the grooves through relative rotation movement of from 5° to 15° of the hook ends with respect to the cup.

19. The inserter system of claim 14 wherein a distal piston of the drive train is extendable through the impaction plate through bore and then releasably connectable to the grasping plate at the grasping plate bore and wherein actuation of the drive train draws the piston in a proximal direction towards the housing, to thereby draw the distal hook ends of the at least two grasping legs and the prosthesis cup in a proximal direction to thereby position the prosthesis cup in a contact relationship against the impaction plate.

20. The inserter system of claim 14 wherein each of the at least two grasping legs comprise a first leg portion and a second leg portion, and wherein the first leg portion forms an angle from 20° to 60° with respect to the longitudinal axis and wherein the second leg portion is distal the first leg portion.

21. The inserter system of claim 14 wherein a space is provided between an outer surface of the nose and an inner surface of the prosthesis cup.

22. The inserter system of claim 14 wherein the drive train of the inserter further comprises:
    a) a first lever comprising a first lever proximal end spaced apart from a first lever distal end located adjacent to the distal housing end;
    b) a second lever comprising a second lever proximal end located adjacent to the proximal housing end and spaced apart from a second lever distal end;
    c) a piston comprising a piston proximal end space apart from a piston distal end releasably connected to the grasping plate, wherein the second lever distal end is in a universal joint relationship with the first lever proximal end, and wherein the first lever distal end is in a universal joint relationship with the piston proximal end and the piston distal end extends through the longitudinally extending bore of the impaction plate of the prosthesis engaging assembly;
    d) a first sleeve pivotably connected to the housing, wherein the first lever is in a slidable relationship with a first opening in the first sleeve disposed at an intermediate location between the first lever proximal end and the first lever distal end; and
    e) wherein the second lever proximal end is manipulable from a first position spaced from the housing to a second position spaced closer to the housing than the first spaced position to cause the second lever to pivot with respect to the housing and thereby move the second lever distal end away from the distal housing end and to further cause the first lever to move away from the distal housing end along the first opening in the first sleeve as the first sleeve pivots on the housing to thereby cause the piston to move along the longitudinal bore in the impaction plate with the prosthesis cup engaged with grasping plate connected to the piston distal end moving from the first position spaced from the impaction plate to the second position closer to the impaction plate than the first position 23. The inserter system of claim 14 wherein the housing is C-shaped.

24. The inserter system of claim 14 wherein a first outer diameter of the grasping plate approximates a second outer diameter of the impaction plate.

25. A surgical kit, which comprises:
    a) at least one inserter according to claim 14;
    b) at least one prosthesis cup; and
    c) a case for organizing components of the kit including the at least one inserter and the at least one prosthesis cup.

26. The inserter system of claim 14 wherein the prosthetic cup implant is a double mobility prosthetic cup implant.

27. A prosthesis engaging assembly, comprising:
    a) an impaction plate comprising an impactor plate central region having a through bore aligned along a longitudinal axis, wherein a plurality of inlets extend from a perimeter of the impaction plate toward, but ending spaced from the impaction plate central region;
    b) a grasping plate positioned along the longitudinal axis distal the impaction plate, wherein the grasping plate is of a unitary, one-piece construction comprising:
        i) a grasping plate central region rigidly supporting at least two spaced apart and outwardly extending grasping legs,
        ii) wherein the grasping plate central region surrounds a grasping plate bore in co-axial alignment with the impactor plate through bore, and
        iii) wherein each of the at least two rigid grasping legs extends from a rigid connection at the grasping plate central region to thereby form a proximal leg portion angle from 20° to 60° with respect to the longitudinal, axis, the proximal leg portion extending to a distal grasping leg portion, and
        iv) wherein one of the distal grasping leg portions is aligned with a respective one of the impaction plate inlets; and
    c) a spring disposed between the impaction plate and the grasping plate,
    d) wherein the grasping plate bore is releasably connectable to a drive train of an inserter for axial movement of the grasping plate including the rigid grasping legs in a proximal direction against a bias of the spring from a first position spaced from the impaction plate to a second position contacting the impaction plate with the rigid grasping legs received in respective ones of the impaction plate inlets.

28. The inserter system of claim 27 wherein a dome-shaped nose is secured to a distal standoff portion of the grasping plate.

29. The inserter system of claim 28 wherein a space is provided between an outer surface of the nose and an inner surface of the prosthesis cup.

* * * * *

UNITED STATES PATENT AND TRADEMARK OFFICE
CERTIFICATE OF CORRECTION

| | | |
|---|---|---|
| PATENT NO. | : 8,961,528 B2 | Page 1 of 1 |
| APPLICATION NO. | : 13/219767 | |
| DATED | : February 24, 2015 | |
| INVENTOR(S) | : Jonas Burgi | |

It is certified that error appears in the above-identified patent and that said Letters Patent is hereby corrected as shown below:

In the Claims

Column 9, line 19 (Claim 4, line 3) delete "Surface" and insert --surface--

Signed and Sealed this
Eighth Day of September, 2015

Michelle K. Lee
*Director of the United States Patent and Trademark Office*